United States Patent
Itakura et al.

(10) Patent No.: US 7,176,700 B2
(45) Date of Patent: Feb. 13, 2007

(54) MOISTURE SENSOR DEVICE AND SELF-DIAGNOSING METHOD THEREFOR

(75) Inventors: Toshikazu Itakura, Toyota (JP); Toshiki Isogai, Nagoya (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 0 days.

(21) Appl. No.: 11/353,065

(22) Filed: Feb. 14, 2006

(65) Prior Publication Data
US 2006/0186901 A1 Aug. 24, 2006

(30) Foreign Application Priority Data
Feb. 24, 2005 (JP) ............... 2005-049598

(51) Int. Cl.
*G01R 27/26* (2006.01)
*G01N 27/22* (2006.01)

(52) U.S. Cl. .............. 324/689; 324/670; 73/335.04

(58) Field of Classification Search .......... 324/689, 324/686, 658, 649, 600; 73/24.04, 25.04, 73/29.01, 73, 335.06
See application file for complete search history.

(56) References Cited

U.S. PATENT DOCUMENTS

| 5,296,819 | A | * | 3/1994 | Kuroiwa et al. ............ 324/670 |
| 5,557,042 | A | * | 9/1996 | Paukkunen et al. ...... 73/335.03 |
| 5,767,687 | A | * | 6/1998 | Geist ............................ 324/664 |
| 5,814,726 | A | * | 9/1998 | Mitter ....................... 73/335.04 |
| 6,028,310 | A | * | 2/2000 | Atkinson et al. ........ 250/339.13 |
| 6,257,061 | B1 | | 7/2001 | Nonoyama et al. |
| 6,356,087 | B1 | | 3/2002 | Wallrafen |
| 6,883,371 | B2 | * | 4/2005 | Sugaya et al. ............ 73/335.05 |
| 2004/0182153 | A1 | | 9/2004 | Hamamoto |
| 2005/0028588 | A1 | * | 2/2005 | Mitter ....................... 73/335.04 |
| 2005/0188764 | A1 | * | 9/2005 | Itakura et al. ............ 73/335.04 |

FOREIGN PATENT DOCUMENTS

JP A-7-146273 6/1995
JP A-2002-39983 2/2002

* cited by examiner

*Primary Examiner*—Andrew H. Hirshfeld
*Assistant Examiner*—Hoai-An D. Nguyen
(74) *Attorney, Agent, or Firm*—Posz Law Group, PLC

(57) ABSTRACT

A moisture sensor device includes a sensor portion having a capacitance that is varied in accordance with surrounding humidity, a signal processor for processing a detection signal of the sensor portion and outputting the signal corresponding to the humidity, a heating portion for heating the sensor portion, and a controller for controlling heating of the heating portion so that the capacitance of the sensor portion is substantially equal to a value under predetermined humidity at least during a self-diagnosis period.

21 Claims, 4 Drawing Sheets

MOISTURE SENSOR DEVICE AND SELF-DIAGNOSING METHOD THEREFOR

CROSS REFERENCE TO RELATED APPLICATION

This application is based upon and claims the benefit of priority of Japanese Patent Application No. 2005-49598 filed on Feb. 24, 2005, the contents of which is incorporated herein by reference.

TECHNICAL FIELD

The technical field relates to a moisture sensor device having a sensor portion in which capacitance is varied in response to atmospheric humidity, and a signal processor for processing a detection signal from the sensor portion and outputting the signal corresponding to moisture, and a self-diagnosing method for the moisture sensor device.

BACKGROUND

The applicant of this application has proposed a capacitive physical-quantity detection apparatus for detecting a physical quantity on the basis of the capacitance between a pair of electrodes disposed so as to face each other as disclosed in JP-A-2000-81449.

According to this capacitive physical-quantity detection apparatus, a capacitive variation between a movable electrode displaced in accordance with variation of a physical quantity (for example, acceleration) and a fixed electrode disposed so as to face the movable electrode is picked up as a voltage variation in a C-V converting circuit designed as a switched capacitor and then subjected to signal processing, whereby the signal corresponding to the variation of the physical quantity can be output.

Furthermore, a self-diagnosing signal (predetermined voltage) is periodically applied between the movable electrode and the fixed electrode to induce electrostatic force between the movable electrode and the fixed electrode, thereby setting the capacitive physical-quantity detection apparatus to such a state that a pseudo physical quantity is applied to the movable electrode. That is, self-diagnosis can be carried out.

However, in the case of a construction that moisture is detected as a physical quantity, a pair of electrodes disposed so as to face each other are fixedly disposed, and thus even when a predetermined voltage is forcedly applied between the pair of electrodes, it is difficult to set the apparatus to such a state that a pseudo physical quantity is induced. That is, the self-diagnosis cannot be carried out.

SUMMARY

In view of the foregoing problem, it is an object to provide a moisture sensor apparatus that can perform self-diagnosis, and a self-diagnosing method for the moisture sensor apparatus.

In order to attain the above object, a moisture sensor is provided comprising a sensor portion whose capacitance is varied in response to atmospheric humidity, and a signal processor for processing a detection signal of the sensor portion and outputting the signal corresponding to the moisture.

According to a first aspect, the moisture sensor apparatus is further equipped with a heating portion for heating the sensor portion, and a controller for controlling the heating of the heating portion so that the capacitance of the sensor portion is substantially equal to a value under a predetermined moisture at least during a self-diagnosis period.

As described above, a predetermined moisture state can be forcedly established. Accordingly, by comparing the output value at this time and the output value to be taken under this moisture state, the self-diagnosis (failure diagnosis of the sensor device) can be performed.

According to a second aspect, it is preferable that the predetermined moisture is set to substantially 0% RH. However, it is not limited to substantially 0% RH.

According to a third aspect, the sensor portion is equipped with a substrate, a pair of detection electrodes disposed on the surface of the substrate so as to be spaced from each other and face each other, a detector that is provided on the substrate so as to cover the gap between the detection electrodes and whose relative permittivity is varied in accordance with moisture, and a reference capacitance portion that is provided on the same plane as the detection electrodes and has a pair of reference electrodes having substantially the same construction as the detection electrodes, the signal processor is equipped with a switched capacitor type C-V converter for converting the capacitance difference between the capacitance value of the detector and the capacitance value of the reference capacitance portion to the corresponding voltage, and the heating portion comprises a heating element provided on the substrate. In this case, the heating portion can be easily formed by a well-known print technique or semiconductor process. Furthermore, the body of the sensor device can be miniaturized. The heating portion may be provided separately from the sensor portion.

According to a fourth aspect, when the substrate is a semiconductor substrate, the signal processor may be provided to the semiconductor substrate, and the heating element may be constructed as a part of the signal processor. In this case, the element constituting the signal processor is applied as the heating element, and thus the construction can be simplified. An insulating substrate such as a glass substrate, a resin substrate or the like may be used as the substrate. However, when a semiconductor substrate having insulating film is used, the sensor device can be formed by the semiconductor process. Accordingly, the manufacturing cost can be reduced.

According to a fifth aspect, a resistor as a heater electrode that heats by current supply thereto may be applied. In this case, it may be provided below the detection electrodes and the reference electrodes through the insulating layer according to a sixth aspect, or it may be provided on moisture sensitive film according to a seventh aspect.

When the moisture sensitive film is provided, water components in the moisture sensitive film can be quickly evaporated, and a predetermined humid state can be established, so that the self-diagnosing time can be shortened. However, invasion of the water components into the moisture sensitive film and evaporation of the water components from the moisture sensitive film are prevented by the resistor, and thus reduction of the response may be estimated. Accordingly, the resistor may be designed to have moisture permeability according to an eighth aspect.

Furthermore, according to a ninth aspect, the width of the resistor is set to be substantially equal to the width of the facing portions of the detection electrodes and the reference electrodes, and designed to have the corresponding construction of the facing portions. Particularly, in the construction that the resistor is provided below the detection electrodes and the reference electrodes, the detection electrodes are located at high positions by providing the resistor thus constructed, and the amount of the moisture sensitive film interposed between the detection electrodes can be increased, and the capacitance variation can be increased. That is, the sensitivity can be enhanced.

According to a tenth aspect, the resistor may be provided on the same plane as the detection electrodes and the reference electrodes. In this case, the resistor may be formed of the same material as the detection electrodes and the reference electrodes, and thus the manufacturing cost can be reduced. Specifically, according to an eleventh aspect, the resistor may be provided between the pair of detection electrodes and between the pair of reference electrodes. Furthermore, the resistor may be provided around the detection electrodes and the reference electrodes.

The heating element is not limited to the resistor. In the semiconductor substrate, at least one of a transistor and a diode may be applied as the heating element according to a twelfth aspect. In the case of the transistor, the detection electrodes and the reference electrodes may be provided in conformity with gate or drain regions. In the case of the diode, the diodes may be provided around the detection electrodes and the reference electrodes.

According to a thirteenth aspect, it is preferable that a protection film is formed on the substrate so as to cover the detection electrodes and the reference electrodes, and the moisture sensitive film is provided on the protection film. In this case, the electrodes can be surely protected from the water components, and corrosion resistance of each electrode to the water components can be enhanced.

According to fourteenth and fifteenth aspects, the action and effect of the self-diagnosing method of the moisture sensor device are the same as the action and effect of the moisture sensor device according to the first and second aspects, and thus the description thereof is omitted.

BRIEF DESCRIPTION OF THE DRAWINGS

The above and other objects, features and advantages of will become more apparent from the following detailed description made with reference to the accompanying drawings. In the drawings.

DESCRIPTION OF THE PREFERRED EMBODIMENTS

Preferred embodiments will be described hereunder with reference to the accompanying drawings. In these embodiments, a moisture sensor device having a so-called comb-shaped electrode structure is used as a capacitive moisture sensor device.

(First Embodiment)

Figure 1A:
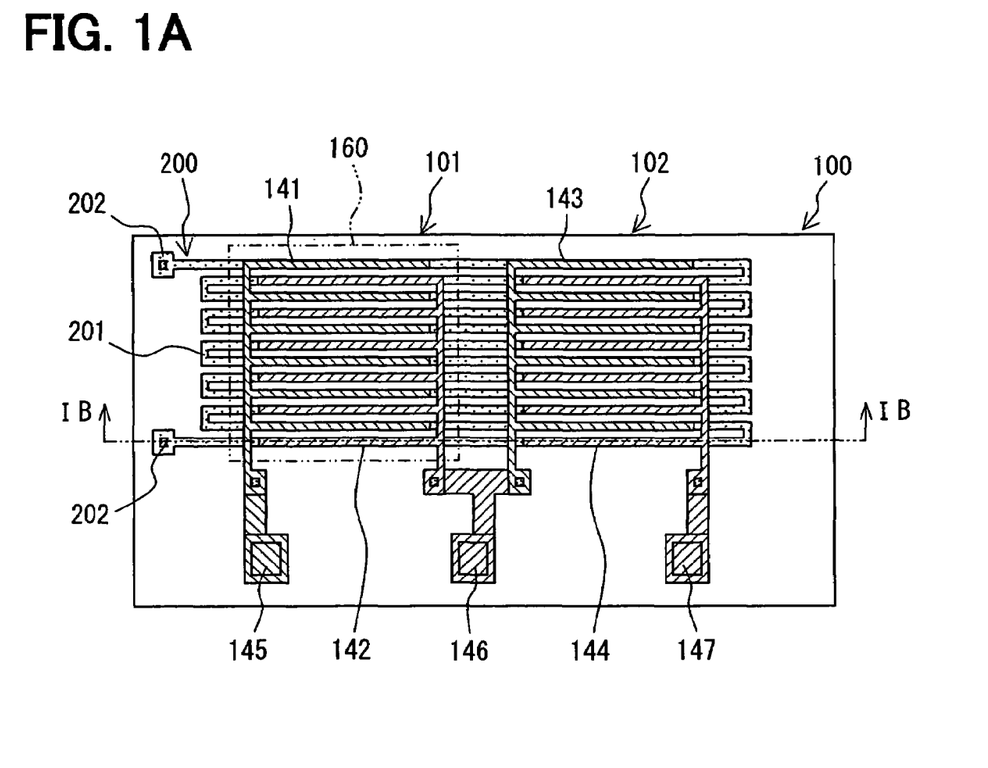
FIG. 1A is an enlarged view showing a sensor portion and a heating portion in a moisture sensor device of an embodiment.
Figure 1B:
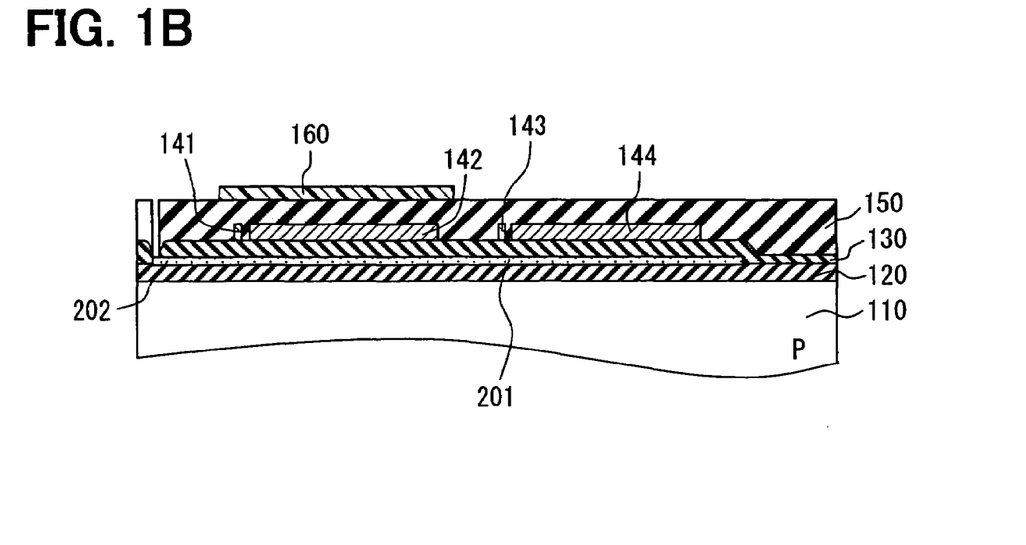
FIG. 1B is a cross-sectional view taken along IB—IB of FIG. 1A.

FIGS. 1A and 1B are enlarged views showing a sensor portion and a heating portion of a moisture sensor device according to an embodiment, wherein FIG. 1A is a plan view and 1B is a cross-sectional view taken along IB—IB. In FIG. 1A, detection electrodes, reference electrodes and a heater electrode are illustrated for the sake of convenience.

As shown in FIG. 1A, a sensor portion 100 comprises a detector 101 whose capacitance is varied in accordance with humidity, and a reference capacitance portion 102 forming reference capacitance. Furthermore, in this embodiment, a heater electrode 201 serving as a heating element is formed as a heating portion 200 on the same substrate as the sensor portion 100. Reference numeral 202 represents pads formed at the end portions of the heater electrode 201.

As shown in FIG. 1B, reference numeral 110 represents a semiconductor substrate as the substrate, and it is formed of p-type silicon in this embodiment. First insulating film 120 (for example, LOCOS (local oxidation of silicon)) is formed on the upper surface of the semiconductor substrate 110. A heater electrode 201 is formed as the heating portion 200 at a predetermined position on the first insulating film 120.

The heater electrode 201 heats at the self-diagnosis time, and it is formed to vaporize water components in moisture sensitive film (described later) constituting the sensor portion 100 to adjust the water amount in the moisture sensitive film, thereby forming a predetermined moisture state. Accordingly, it is preferably formed around the detection portion 101. In this embodiment, in order to offset the effect of the heating, the heater electrode 201 is formed in conformity with not only the detector 101, but also the reference capacitance portion 102. The shape of the heater electrode 201 will be described later.

Any material may be used as the material of the heater electrode 201 insofar as it is heated by current supply thereto. However, in order to shorten the self-diagnosis time, it is preferable that the material has a sheet resistance value of several Ω or more, and for example, a wiring material such as polysi, Cr—Si or the like may be applied. At this time, the above wiring material may be deposited on the first insulating film 120 by vapor deposition, sputtering or other methods, and then patterned by a photolithography treatment. In this embodiment, the heater electrode 201 is formed by using polysi.

Second insulating film 130 (for example, silicon oxide film) is formed on the first insulating film 120 containing the heater electrode 201, and a pair of detection electrodes 141, 142 are disposed on the same plane as the second insulating film 130 so as to be spaced from each other.

The shape of the detection electrodes 141, 142 is not limited to a specific one. However, in this embodiment, a comb-shape is adopted as the shape of the detection electrodes 141, 142 as shown in FIG. 1A. By setting the shape to the comb-shape as described above, the facing areas of the detection electrodes 141, 142 can be increased while reducing the arrangement area of the detection electrodes 141, 142. Accordingly, the variation amount of the electrostatic capacitance between the detection electrodes 141, 142 which varies in connection with the surrounding humidity variation is increased, and the sensitivity of the moisture sensor device can be enhanced.

The detection electrodes 141, 142 are formed by depositing a wiring material such as aluminum, copper, gold, platinum, polySi or the like on the semiconductor substrate 110 by a manner such as vacuum deposition, sputtering or the like, and then patterning the wiring material into a comb-shaped pattern through a photolithography treatment. In this embodiment, the detection electrodes 141, 142 are formed by using aluminum.

Furthermore, a pair of reference electrodes 143, 144 are disposed within the same plane on the second insulating film 130 adjacently to the detection electrodes 141, 142 so as to be spaced from each other and face each other. The reference electrodes 143, 144 are formed of the same material as the detection electrodes 141, 142 and designed to have the same pattern. In FIG. 1A, reference numeral 145 represents a pad for the detection electrode 141, reference numeral 146 represents a common pad for the detection electrode 142 and the reference electrode 143, and reference numeral 147 represents a pad for the reference electrode 144.

Figure 2A:
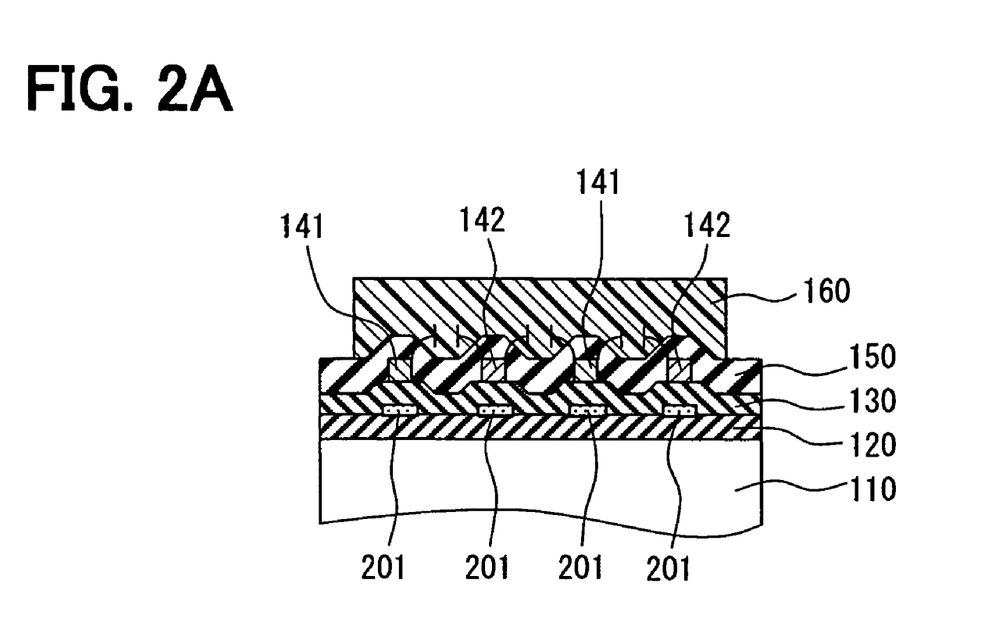
FIG. 2A is a cross-sectional view showing a case where a heater electrode is disposed.

Silicon nitride film is formed as protection film 150 on the semiconductor substrate 110 so as to cover the detection electrodes 141, 142 and the reference electrodes 143, 144. The protection film 150 is deposited and formed by a plasma CVD method or the like so as to have the same thickness at the respective parts on the semiconductor substrate 110. When the detection electrodes 141, 142 and the reference electrodes 143, 144 have corrosion resistance to the water components, it is unnecessary to form the protection film 150. In FIG. 2A, the protection film is omitted for the sake of convenience.

Moisture sensitive film 160 that is formed of polyimide-based polymer or the like and has a moisture-absorption characteristic is formed on the protection film 150 so as to cover the detection electrodes 141, 142 and the gaps between the detection electrodes 141, 142. The moisture sensitive film 160 can be formed by coating precursors (polyamide acid) of polyimide-based polymer by a spin coat method, a print method or the like and then heating and hardening the precursors.

When water components infiltrate into the moisture sensitive film 160, the relative permittivity of the moisture sensitive film 160 varies in accordance with the amount of the infiltrating water components because water has a large relative permittivity. As a result, the electrostatic capacitance of a capacitor that is constructed by the detection electrodes 141, 142 with the moisture sensitive film 160 as a part of the dielectric material is varied. On the other hand, no moisture sensitive film 160 is provided to the reference electrodes 143, 144, and thus the electrostatic capacitance of the capacitor constructed by the reference electrodes 143, 144 is not varied, or even when it varies, the variation is slight. The water amount contained in the moisture sensitive film 160 corresponds to the humidity around the sensor portion 100, and thus the humidity can be detected on the basis of the capacitance difference of the electrostatic capacitance between the detection electrodes 141, 142 and the electrostatic capacitance between the reference electrodes 143, 144. The site having the above construction excluding the heater electrode 201 corresponds to the sensor portion 100, and the site containing the detection electrodes 141, 142 and the moisture sensitive film 160 corresponds to the detection portion 101, and the site containing the reference electrodes 143 and 144 corresponds to the reference capacitance portion 102.

Furthermore, in this embodiment, the detection electrodes 141, 142 and the reference electrodes 143, 144 are formed of the same material and designed to have the same pattern as described above, and the corresponding comb teeth are disposed adjacently to one another so as to be located on the same line. As shown in FIG. 1A, the heater electrode 201 has substantially the same electrode width as the facing portions (capacitor constituting portion) of the detection electrodes 141, 142 and the reference electrodes 143, 144, and is designed in a meandering shape so as to be located just below the facing portions through the second insulating film 130.

Figure 2B:
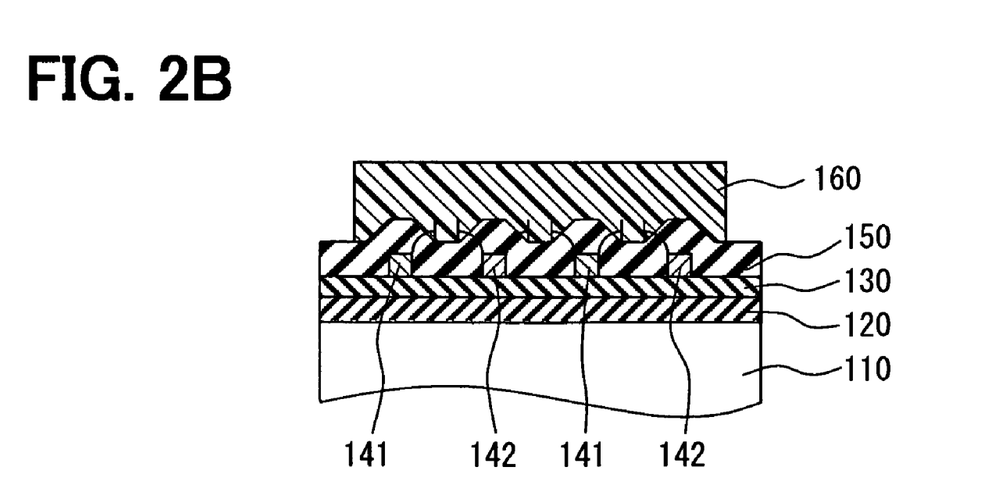
FIG. 2B is a cross-sectional view showing a case where no heater electrode is disposed.

When the heater electrode 201 is formed just below the confronting portions of the detection electrodes 141, 142 as described above (FIG. 2A), recesses are formed in the protection film 150 and thus the amount of the moisture sensitive film 160 interposed between the detection electrodes 141, 142 is more increased as compared with a case where no heater electrode 201 is formed in the above construction (FIG. 2B) or a case where the heater electrode 201 is not disposed just below the facing portions of the detection electrodes 141, 142, but they are disposed in the meandering arrangement with respect to the facing portions of the detection electrodes 141, 142. That is, the sensitivity can be enhanced with increasing the area of the detection electrodes 141, 142. FIGS. 2A and 2B are cross-sectional views showing the effect of the arrangement of the heater electrode 201, and particularly, FIG. 2A is a diagram when the heater electrode 201 is provided, and FIG. 2B is a diagram when no heater electrode 201 is provided.

Figure 3:
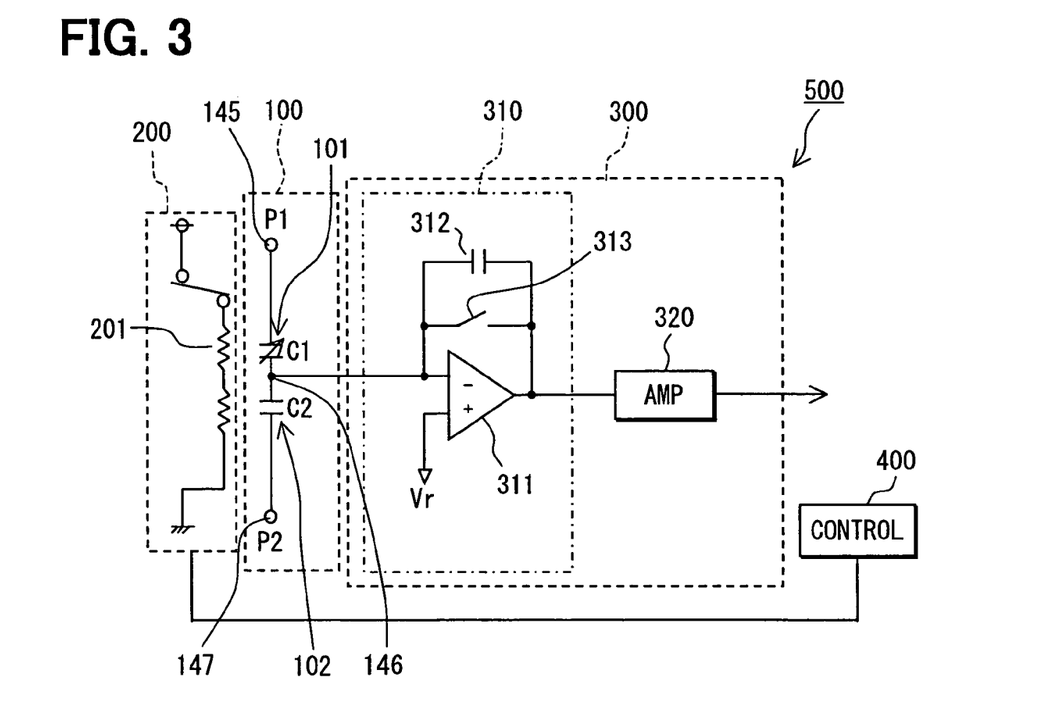
FIG. 3 is a diagram showing a construction of the moisture sensor device that can perform self-diagnosis.

Next, the construction of a moisture sensor device 500 that can perform self-diagnosis will be described with reference to FIG. 3. In this embodiment, a signal processor 300 and a controller 400 for controlling the heating of the heater electrode 201 constituting the heating portion 200 are constructed on a substrate different from the sensor portion 100.

The signal processor 300 is equipped with at least a switched capacitor type C-V converter 310, and an amplifying portion 320.

The C-V converter 310 comprises an operational amplifier 311, a feedback capacitor 312 having a capacitance value Cf and a switch 313. The charge corresponding to the difference between the charge proportional to the capacitance value C1 occurring between the detection electrodes 141 and 142 constituting the detector 101 and the charge proportional to the capacitance value C2 occurring between the reference electrodes 143, 144 constituting the reference portion 102 is accumulated in the feedback capacitor 312 and converted to the corresponding voltage, and then the voltage thus converted is output.

The inverted input terminal of the operational amplifier 311 is connected to the detection electrode 142 and the reference electrode 143 through the pad 146, and a feedback capacitor 312 and a switch 313 are connected in parallel between the inverted input terminal and the output terminal of the operational amplifier 311. Furthermore, a reference voltage generating circuit (not shown) for applying a reference voltage Vr is connected to the non-inverted input terminal.

Furthermore, the signal processor 300 has a driving voltage generating circuit (not shown). The driving voltage generating circuit inputs a carrier wave P1 periodically varying at a fixed amplitude (0 to V) from the pad 145 to the detection electrode 141 of the detector 101, and inputs, from the pad 147 to the reference electrode 144 of the reference portion 102, a carrier wave P2 that is displaced from the carrier wave P1 in phase by 180 degrees and has the same amplitude.

The switch 313 is turned on/off on the basis of a trigger signal which is generated in synchronism with a clock signal from the driving voltage generating circuit, and for example it is set so as to be turned on for only a fixed time (a time shorter than the half period of the carrier wave P1) at the rise-up timing of the carrier wave P1 (the falling timing of the carrier P2).

During a detection period T1, the switch 313 is turned on. The feedback capacitor 312 is discharged, and reset to the reference voltage Vr. Subsequently, the switch 313 is turned off, and the reset operation is completed. Next, when the carrier waves P1, P2 are inverted, the charge of (C1−C2)×V is discharged from the gap between the detection electrodes 141, 142 and between the reference electrodes 143, 144, and this charge is accumulated in the feedback capacitor 312. Accordingly, the voltage Vs corresponding to the capacitance difference (C1−C2) and the amplitude V of the sensor portion 100 occurs with the reference voltage Vr as a reference occurs at the output terminal of the operational amplifier 311. The voltage Vr is represented by the following equation.

$$Vs=(C1-C2)/Cf \times V+Vr \quad \text{(equation 1)}$$

At this time, with the variation of the surrounding humidity, the capacitance value C2 of the reference portion 62 is not varied, or even when it is varied, the variation is slight. The capacitance value C1 of the detector 61 is varied. Accordingly, by detecting the voltage Vs shown in table 1, the humidity can be detected.

The amplifying portion 320 amplifies the output voltage Vs of the C-V converter 310 to a predetermined sensitivity. As not shown, a sampling hold portion for sampling the output voltage Vs of the C-V converter 310 and holding the output voltage Vs thus hold for a fixed term may be provided just before the amplifying portion 320, and also a low pass filter for taking out only the components of a predetermined frequency band from the output voltage of the amplifying portion 320 may be provided just after the amplifying portion 320.

Here, the self-diagnosis is carried out as follows.

Under the state that driving voltages (carrier waves P1, P2) are applied to the detection electrodes 141, 142 and the reference electrodes 143, 144 of the sensor portion 100, the controller 400 outputs a self-diagnosing signal to the heating portion 200 every predetermined period, for example.

When the self-diagnosing signal is received in the heating portion 200, the heater electrode 201 is supplied with current and generates heat. In this embodiment, it is designed so that the heater electrode 201 is supplied with current and generates heat during the period when the self-diagnosing signal is output from the controller 400, whereby the capacitance (capacitance difference) of the sensor portion 100 is controlled to be equal to the value at substantially 0% RH. The amount of water evaporated from the moisture sensitive film 160 (the amount of water in the moisture sensitive film 160) is adjusted by the heating value of the heater electrode 201 (that is, the moisture state is adjusted), and thus the moisture state can be adjusted to a moisture state other than the substantially 0% RH moisture state. However, it is necessary to control the heating value of the heater electrode 201 at the self-diagnosis time in accordance with the sensor output at the normal detection time, and thus the construction of the device can be simplified. On the other hand, in this embodiment, the heating amount is set (the output time of the self-diagnosis signal) so that the substantially 0% RH state is established at all times irrespective of the sensor output at the normal detection time, whereby the self-diagnosis can be surely performed.

In this embodiment, the heater electrode 201 is disposed in connection with the detection electrodes 141, 142 and the reference electrodes 143, 144 that have the same construction, and thus the effect of the heating (hot characteristic) can be offset.

The output of the sensor portion 100 under the state that the water amount in the moisture sensitive film 160 is adjusted, that is, the moisture state is adjusted is converted to the corresponding voltage in the C-V converter 310, and the voltage thus converted is amplified to a predetermined sensitivity and then output in the amplifying portion 320. By subjecting the output signal to comparison and judgment according to a predetermined logic in ECU (Electric Control Unit), for example, self-diagnosis on whether there is any abnormality (for example, characteristic variation caused by adhesion of foreign matters, abnormality of moisture sensitive film, failure of the signal processor, etc.) of the device 500 can be performed.

In this embodiment, the comparison and judgment is carried out in ECU. However, it may be designed so that a comparing portion (for example, a construction having a comparator) is equipped as a part of the signal processor 300, and the comparison is carried out in the device 500. The output line from the amplifying portion 320 may be switched between a normal test line and a self-diagnosis line containing the comparator by, for example, the presence or absence of the self-diagnosis signal from the controller 400.

Furthermore, in this embodiment, the signal processor 300 is constructed on the substrate different from the sensor portion 100. However, it may be constructed on the same substrate. An insulating substrate such as a glass substrate or the like may be used as the substrate, however, the semiconductor process can be actively used by using a semiconductor substrate 110 having the insulating film as described in this embodiment. Accordingly, the manufacturing cost can be reduced. At this time, the heater electrode 201 as the heating element can be integrated with the signal processor 300.

(Second Embodiment)

Figure 4:
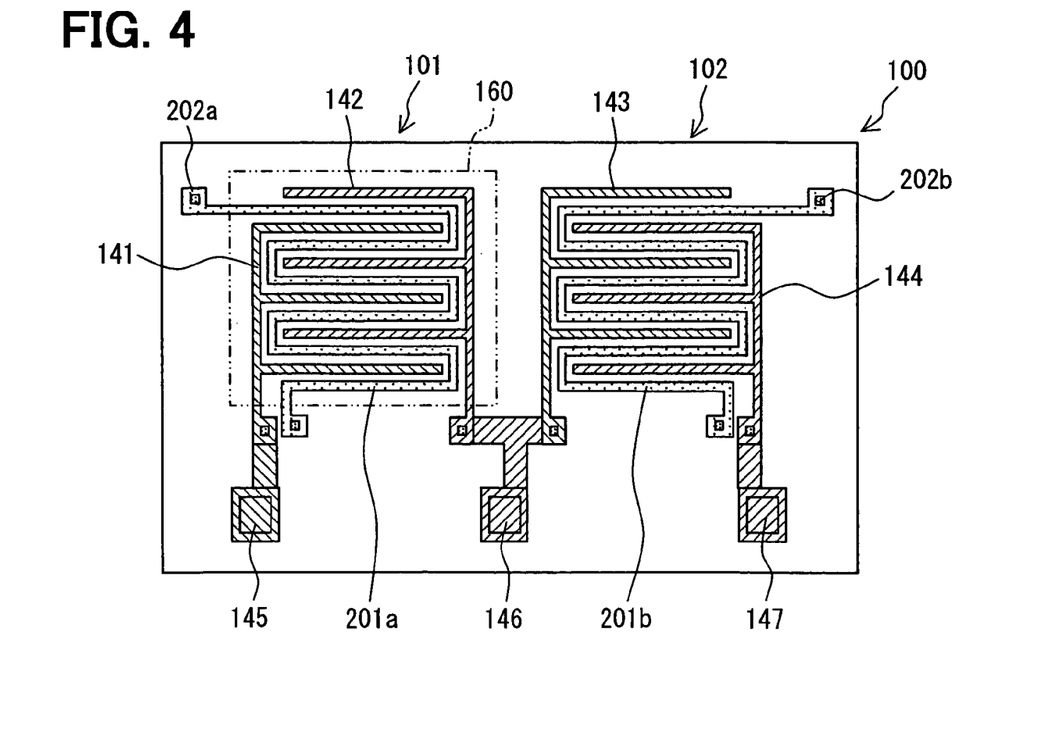
FIG. 4 is an enlarged plan view showing a sensor portion and a heating portion in a moisture sensor device according to a second embodiment of the present invention.

Next, a second embodiment will be described with reference to FIG. 4. FIG. 4 is an enlarged plan view showing a sensor portion and a heating portion in a moisture sensor device of this embodiment, and it corresponds to FIG. 1A of the first embodiment. For the sake of convenience, the detection electrodes, the reference electrodes and the heater electrode are shown.

The moisture device of the second embodiment has many common elements to the first embodiment. Therefore, the detailed description of the common parts is omitted, and emphasis will be placed on description of the different parts.

As shown in FIG. 4, heater electrodes 201a, 201b are constructed on the same plane as the detection electrodes 141, 142 and the reference electrodes 143, 144. Accordingly, when the heater electrodes 201a, 201b are formed of the same constituent material as the detection electrodes 141, 142 and the reference electrodes 143, 144, the manufacturing process can be simplified. In FIG. 4, reference numerals 202a, 202b represent pads for the heater electrodes 201a, 201b.

Furthermore, in this embodiment, the heater electrode 201a is provided at the intermediate site between the detection electrodes 141, 142, and the heater electrode 201 b is provided at the intermediate site between the reference electrodes 143, 144. Out of the self-diagnosis time (normal detection time), the heater electrodes 201a and 201b are kept to the intermediate potentials of the voltages applied to the detection electrodes 141, 142 and the reference electrodes 143, 144. Accordingly, at the normal detection time, the capacitance balance between the detection electrodes 141, 142 and the capacitance balance between the reference electrodes 143, 144 can be kept although the heater electrode 201a is disposed between the detection electrodes 141, 142 and the heater electrode 201b is disposed between the reference electrodes 143 and 144. Furthermore, the heater electrodes 201a, 201b are designed as a bridge construction so that no heat is generated at the normal detection time.

In this embodiment, the heater electrode 201a is provided between the detection electrodes 141, 142, and the heater electrode 201b is provided between the reference electrodes 143, 144. However, only one heater electrode 201 may be provided.

Furthermore, in the above embodiment, the heater electrode 201a is provided between the detection electrodes 141, 142 and heater electrode 201b is provided between the reference electrodes 143, 144. However, when the above construction is adopted, the facing distance between the detection electrodes 141, 142 and the facing distance between the reference electrodes 143, 144 are lengthened, so that the sensitivity is reduced. Therefore, the heater electrodes 201a, 201b may be provided around of the detection electrodes 141, 142 and the reference electrodes 143, 144. In this case, each of the heater electrodes 201a, 201b may be further divided.

(Third Embodiment)

Figure 5:
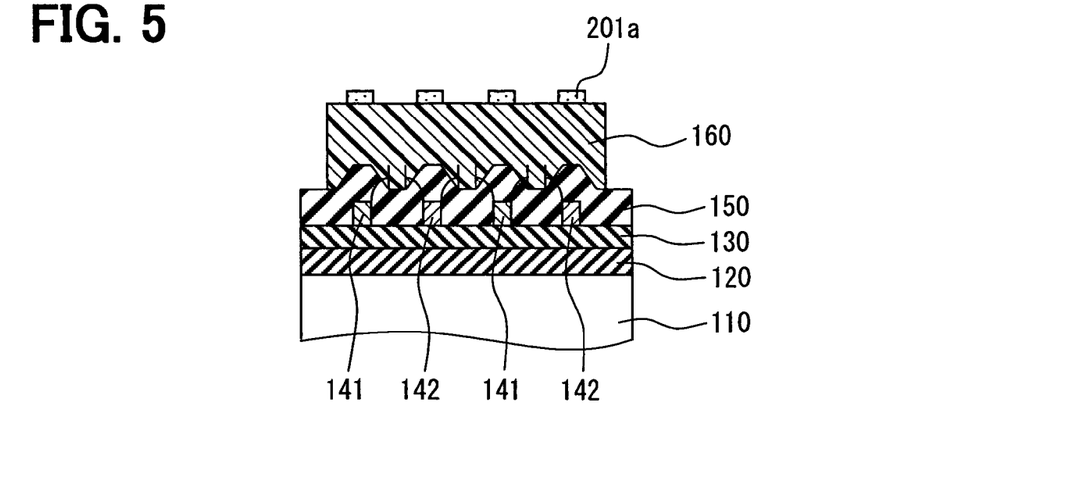
FIG. 5 is an enlarged cross-sectional view of the surrounding of a detection portion of a moisture sensor device according to a third embodiment.

Next, a third embodiment according will be described with reference to FIG. 5. FIG. 5 is an enlarged cross-sectional view showing the surrounding of the detector, and it corresponds to FIG. 2A of the first embodiment.

The moisture sensor device of the third embodiment has many common parts to the first embodiment. Therefore, the detailed description of the common parts is omitted, and emphasis will be placed on description of the different parts.

As shown in FIG. 5, in this embodiment, the heater electrode 201a is provided on the moisture sensitive film 160. With this construction, the moisture sensitive film 160 is directly heated, and thus the water components in the moisture sensitive film 160 can be quickly vaporized to establish a predetermined moisture state. Therefore, the self-diagnosis time can be shortened. Since the heater electrode 201a is provided on the moisture sensitive film 160, this embodiment is constructed so that the heater electrode 201a is shared by the detector 101 and the reference capacitance portion 102.

However, it is considered that the invasion of the water component into the moisture sensitive film 160 and the vaporization of the water components from the moisture sensitive film 160 are prevented by the heater electrode 201a, and thus the response is lowered. Therefore, in this embodiment, the heater electrode 201a is provided with moisture permeability. Specifically, a thin film of metal material is deposited (for example, 0.1 µm) on the moisture sensitive film 160 by a vacuum deposition method to form the heater electrode 201a. Accordingly, water molecules can transmit between the metal atoms of the heater electrode 201a which is formed as thin film.

Furthermore, in this embodiment, the heater electrode 201a is disposed just above the facing portions of the detection electrodes 141 and 142. Accordingly, as compared with the case where the heater electrode 201a is disposed in the meandering form with respect to the facing portions of the detection electrodes 141, 142, water molecules can more easily income to and outgo from the area of the moisture sensitive film 160 which presents between the detection electrodes 141, 142 and contributes to the capacitance variation. That is, the response can be enhanced.

(Fourth Embodiment)

Figure 6:
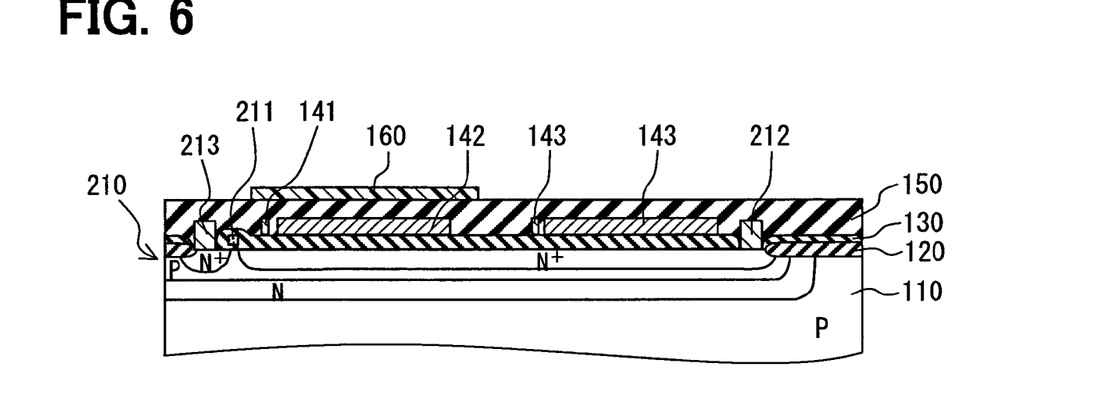
FIG. 6 is an enlarged cross-sectional view showing a sensor portion and a heating portion in a moisture sensor device according to a fourth embodiment.

Next, a fourth embodiment will be described with reference to FIG. 6. FIG. 6 is an enlarged cross-sectional view showing a sensor portion and a heating portion in a moisture sensor device according to this embodiment.

The moisture sensor device of the fourth embodiment has many common parts to the first embodiment. Therefore, the detailed description of the common parts is omitted, and emphasis will be placed on describing the different parts.

In the first to third embodiments, the heater electrode 201 (201a, 201b) is applied as the heating portion 200. However, the heating portion 200 is not limited to the heater electrode 201. In the semiconductor substrate 110, at least one of the transistor and the diode which constitute the signal processor 300 may be applied. In this case, it is unnecessary to provide the heater electrode 201 separately, and thus the manufacturing process can be simplified.

For example, in the case of the transistor, at least the facing portions of the detection electrodes 142, 143 and the reference electrodes 143, 144 may be provided on the diffusion area as shown in FIG. 6. In FIG. 6, reference numeral 210 represents a MOS transistor, reference numeral 211 represents a gate electrode formed of polySi, reference numeral 212 represents a drain electrode, and reference numeral 213 represents a source electrode, and the detection electrodes 141, 142 and the reference electrodes 143, 144 are provided on the $N^+$ drain region.

In the case of the diode, a diode is provided around the detection electrodes and the reference electrodes.

The present invention is not limited to the above embodiments, and various modifications may be made.

Furthermore, in the above embodiment, the semiconductor substrate 110 formed of silicon is applied as the substrate. However, an insulating substrate such as a glass substrate, a resin substrate or the like may be applied as the substrate.

In this embodiment, the moisture sensitive film 160 is provided on the protection film 150. However, when no protection film 150 is formed, the moisture sensitive film 160 may be formed on the second insulating film 130. Furthermore, when the substrate comprises an insulating substrate such as a glass substrate or the like, the moisture sensitive film 160 may be directly formed on the insulating substrate.

Furthermore, in this embodiment, the detection electrodes 141, 142 and the reference electrodes 143, 144 are designed in a comb-shaped structure. However, the structure of each electrode forming the capacitance is not limited to the above embodiment. For example, they may be designed in a so-called parallel flat plate type structure. Furthermore, the detection electrode 141, 142 and the reference electrode 143, 144 may be designed in different structures.

In short, any construction may be adopted in the present invention insofar as it comprises the sensor portion 100 whose capacitance is varied in accordance with the surrounding humidity, the heating portion 200 for heating the sensor portion, the signal processor 300 for processing the detection signal of the sensor portion 100 and outputting the signal corresponding to the humidity, and the controller 400 for controlling the heating of the heating portion 200 so that the capacitance of the sensor portion 100 is substantially equal to a value under a predetermined humidity at least during a self-diagnosis period. The above elements may be separately provided, or all the elements may be integrally formed in the same substrate.

Figure 7:
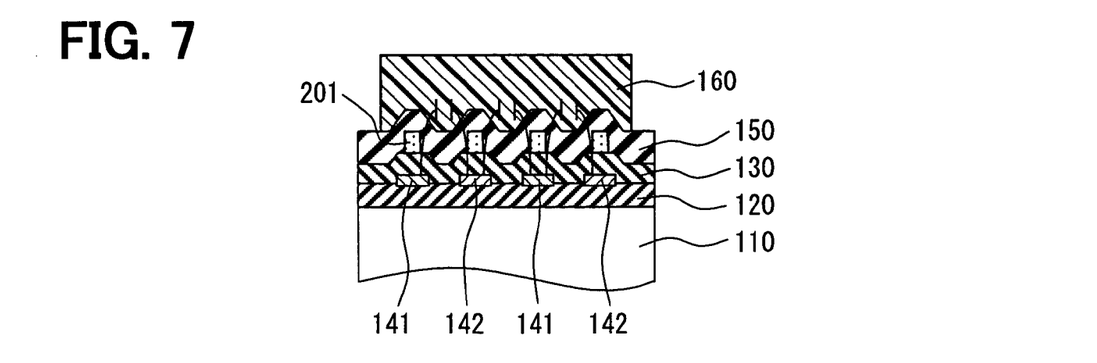
FIG. 7 is an enlarged cross-sectional view of the surrounding of a detection portion of another modification.

Furthermore, in the embodiments, the heater electrode 201 is provided through the second insulating film 130 just below the detection electrodes 141, 142 (and the reference electrodes 143, 144). However, as shown in FIG. 7, the detection electrodes 141, 142 (and the reference electrodes 143, 144) may be provided just below the heater electrode 201 through the second insulating film 130. In this case, water molecules in the moisture sensitive film 160 can be quickly vaporized, and thus the self-diagnosing time can be shortened. However, the amount of the moisture sensitive film 160 that is interposed between the detection electrodes 141, 142 and contributes to the capacitance variation is reduced, and thus the sensitivity is lowered. Accordingly, the construction of the first embodiment is more preferable.

The invention claimed is:

1. A moisture sensor device comprising:
   a sensor portion having a capacitance that is varied in accordance with surrounding humidity;
   a signal processor for processing a detection signal of the sensor portion and outputting the signal corresponding to the humidity;
   a heating portion for heating the sensor portion; and
   a controller for controlling beating of the heating portion so that the capacitance of the sensor portion is substantially equal to a value under predetermined humidity at least during a self-diagnosis period;
   wherein the sensor portion comprises a substrate, a pair of detection electrodes disposed on the surface of the substrate so as to be spaced from each other and face each other, a detector that is provided on the substrate so as to cover the gap between the detection electrodes and whose relative permittivity is varied in accordance with moisture, and a reference capacitance portion that is provided on the same plane as the detection electrodes and has a pair of reference electrodes having substantially the same construction as the detection electrodes;
   wherein the signal processor is equipped with a switched capacitor type C-V converter for converting the capacitance difference between the capacitance value of the detector and the capacitance value of the reference capacitance portion to the corresponding voltage;
   wherein the heating portion comprises a heating element provided on the substrate;
   wherein the heating element comprises a resistor as a heater electrode that is supplied with current to generate heat:
   wherein the resistor is provided below the detection electrodes and the reference electrodes through an insulating layer;
   wherein the resistor has substantially the same width as facing portions of the detection electrodes and the reference electrodes, and are provided in connection with the facing portions.

2. The moisture sensor device according to claim 1, wherein the predetermined humidity is substantially equal to 0% RH.

3. The moisture sensor device according to claim 1, wherein the substrate comprises a semiconductor substrate, the signal processor is provided on the semiconductor substrate, and the heating element is constructed as a part of the signal processor.

4. The moisture sensor device according to claim 1, wherein the resistor is provided on the moisture sensitive film.

5. The moisture sensor device according to claim 4, wherein the resistor has moisture permeability.

6. The moisture sensor device according to claim 3, wherein the heating element comprises at least one of a transistor and a diode.

7. The moisture sensor device according to claim 3, wherein the heating element comprises a resistor as a heater electrode that is supplied with current to generate heat.

8. A moisture sensor device comprising:
   a sensor portion having a capacitance that is varied in accordance with surrounding humidity;
   a signal processor for processing a detection signal of the sensor portion and outputting the signal corresponding to the humidity;
   a heating portion for heating the sensor portion; and
   a controller for controlling heating of the heating portion so that the capacitance of the sensor portion is substantially equal to a value under predetermined humidity at least during a self-diagnosis period,
   wherein the sensor portion comprises a substrate, a pair of detection electrodes disposed on the surface of the substrate so as to be spaced from each other and face each other, a detector that is provided on the substrate so as to cover the gap between the detection electrodes and whose relative permittivity is varied in accordance with moisture, and a reference capacitance portion that is provided on the same plane as the detection electrodes and has a pair of reference electrodes having substantially the same construction as the detection electrodes;
   wherein the signal processor is equipped with a switched capacitor type C-V converter for converting the capacitance difference between the capacitance value of the detector and the capacitance value of the reference capacitance portion to the corresponding voltage;
   wherein the heating portion comprises a heating element provided on the substrate;
   wherein the heating element comprises a resistor as a heater electrode that is supplied with current to generate heat;
   wherein the resistor is provided on the same plane as the detection electrodes and the reference electrodes;
   wherein the resistor is provided between the pair of detection electrodes and between the pair of reference electrodes.

9. The moisture sensor device according to claim 8, wherein the predetermined humidity is substantially equal to 0% RH.

10. The moisture sensor device according to claim 8, wherein the substrate comprises a semiconductor substrate, the signal processor is provided on the semiconductor substrate, and the heating element is constructed as a part of the signal processor.

11. The moisture sensor device according to claim 8, wherein the resistor is provided on the moisture sensitive film.

12. The moisture sensor device according to claim 11, wherein the resistor has moisture permeability.

13. The moisture sensor device according to claim 10, wherein the heating element comprises at least one of a transistor and a diode.

14. The moisture sensor device according to claim 10, wherein the heating element comprises a resistor as a heater electrode that is supplied with current to generate heat.

15. A moisture sensor device comprising:
a sensor portion having a capacitance that is varied in accordance with surrounding humidity;
a signal processor for processing a detection signal of the sensor portion and outputting the signal corresponding to the humidity;
a heating portion for heating the sensor portion;
a controller for controlling heating of the heating portion so that the capacitance of the sensor portion is substantially equal to a value under predetermined humidity at least during a self-diagnosis period; and
wherein the sensor portion comprises a substrate, a pair of detection electrodes disposed on the surface of the substrate so as to be spaced from each other and face each other, a detector that is provided on the substrate so as to cover the gap between the detection electrodes and whose relative permittivity is varied in accordance with moisture, and a reference capacitance portion that is provided on the same plane as the detection electrodes and has a pair of reference electrodes having substantially the same construction as the detection electrodes;
wherein the signal processor is equipped with a switched capacitor type C-V converter for converting the capacitance difference between the capacitance value of the detector and the capacitance value of the reference capacitance portion to the corresponding voltage; and
wherein the heating portion comprises a heating element provided on the substrate; and a protection film formed on the substrate so as to cover the detection electrodes and the reference electrodes, wherein the moisture sensitive film is provided on the protection film.

16. The moisture sensor device according to claim 15 wherein the predetermined humidity is substantially equal to 0% RH.

17. The moisture sensor device according to claim 15, wherein the substrate comprises a semiconductor substrate, the signal processor is provided on the semiconductor substrate, and the heating element is constructed as a part of the signal processor.

18. The moisture sensor device according to claim 15, wherein the resistor is provided on the moisture sensitive film.

19. The moisture sensor device according to claim 18, wherein the resistor has moisture permeability.

20. The moisture sensor device according to claim 17, wherein the heating element comprises at least one of a transistor and a diode.

21. The moisture sensor device according to claim 17, wherein the heating element comprises a resistor as a heater electrode that is supplied with current to generate heat.

* * * * *